(12) United States Patent
McKnight et al.

(10) Patent No.: US 8,101,388 B2
(45) Date of Patent: Jan. 24, 2012

(54) METHOD AND STRUCTURE FOR EXTRACTING MOLECULAR SPECIES

(75) Inventors: Timothy E. McKnight, Greenback, TN (US); Anatoli V. Melechko, Oak Ridge, TN (US); Michael L. Simpson, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 1120 days.

(21) Appl. No.: 11/904,862

(22) Filed: Sep. 28, 2007

(65) Prior Publication Data

US 2009/0087899 A1    Apr. 2, 2009

(51) Int. Cl.
*C12N 13/00* (2006.01)
*C12P 1/00* (2006.01)
*C12P 21/00* (2006.01)
*C12M 1/00* (2006.01)

(52) U.S. Cl. .......... 435/173.4; 435/267; 435/283.1; 435/70.3

(58) Field of Classification Search .......... None
See application file for complete search history.

(56) References Cited

U.S. PATENT DOCUMENTS 6,982,519 B2   1/2006  Guillorn et al.
7,144,287 B2   12/2006 Guillorn et al.
7,229,692 B2   6/2007  Melechko et al.
2002/0175323 A1 11/2002 Guillom et al.
2004/0197909 A1 10/2004 McKnight et al.

FOREIGN PATENT DOCUMENTS
WO    WO 01/67821    9/2001

OTHER PUBLICATIONS

Cai, H., et al., "Carbon Nanotube-Enhanced Electrochemical DNA Biosensor for DNA Hybridization Detection", *Anal Bioanal Chem* 375: 287-293 (2003).
Wong, S.S. et al., "Covalently Functionalized Nanotubes as Nanometresized Probes in Chemistry and Biology", *Nature* 394:52-55 (1998).
Li, W.Z. et al., "Large-Scale Synthesis of Aligned Carbon Nanotubes", *Science* 274: 1701-1703 (1996).

*Primary Examiner* — Chris R Tate
*Assistant Examiner* — Aaron J Kosar
(74) *Attorney, Agent, or Firm* — Scully, Scott, Murphy & Presser, P.C.

(57) ABSTRACT

The present invention in one embodiment provides a method for extracting molecular material including providing a probe comprising a penetration portion having a nanoscale surface for penetrating a biological compartment, a receptor present on the penetrating portion of the probe, wherein the receptor has an affinity for a target molecular material from the biological compartment; inserting the probe into the biological compartment, the receptor present on the penetrating portion of the probe engages the target molecular material; and extracting the probe and the target molecular material engaged to the inserting portion of the probe from the biological compartment.

18 Claims, 6 Drawing Sheets

METHOD AND STRUCTURE FOR EXTRACTING MOLECULAR SPECIES

FIELD OF THE INVENTION

The present invention relates generally to the field of nanotechnology. In one embodiment, the invention relates to methods and devices for extracting molecular materials from biological compartments, such as cells.

BACKGROUND OF THE INVENTION

Efficient manipulation of biological systems at the subcellular and molecular scale is desired to enable mankind to further its knowledge of cellular processes and to enhance our ability to modify and control cellular function. A number of applications require the extraction and purification of intracellular molecular species; including but not limited to gene arrays (mRNA extraction), protein discovery (structure and functional from physical attributes), clinical biopsy of tissue (presence or absence of specific proteins), cancer diagnostics (via quantitation of over or under production of specific proteins), protein extraction and purification for purposes of discovering protein function and the regulatory pathways associated with the protein, sampling of cells for viral infection, commercial production of polymerase, commercial production of proteins and enzymes, commercial production of co-factors.

Traditionally, extraction and purification is approached by lysing cells and purifying the lysate. As such, the target material is typically altered from its 'native' intracellular state, due to dramatic changes that occur to the environment during lysis and purification. Also due to lysis and therefore death of cells, the extraction can only be performed once for any given group of cells, wherein resampling of the cell population is not an option. Further, the lysed cells cannot be propagated further to yield more product, or to provide verification of the results of the extraction.

SUMMARY OF THE INVENTION

The present invention, in one embodiment provides methods and structures for extracting molecular material from a biological compartment. In one embodiment, the method of extracting molecular material includes:
providing a probe comprising a penetration portion having a nanoscale surface for penetrating a biological compartment, a receptor present on the penetrating portion of the probe, wherein the receptor has an affinity for a target molecular material;
inserting the probe into the biological compartment, wherein the receptor present on the penetrating portion of the probe engages the target molecular material; and
extracting the probe and the target molecular material engaged to the receptor on the inserting portion of the probe from the biological compartment.

In one embodiment, the biological compartment from which the targeted molecule species may be extracted is a cell having a diameter of greater than about 500 nm. In one embodiment, the cell has a diameter ranging from about 500 nm to about 100 microns. In another embodiment, the biological compartment is the intercellular space between at least two cells in a tissue.

In one embodiment, the probe may be constructed of at least one carbon nano-fiber, carbon nano-tube, silicon dioxide nano-tube, silicon, silicon dioxide micro-machined needle or combination thereof.

In one embodiment, the receptor is composed of DNA, proteins, RNA, peptide nucleic acids or combinations thereof. In one embodiment, the receptor comprises a tetR protein and the target molecular material comprises a tetO operator. In another embodiment, the receptor comprises Gamma-H2AX and the target molecular material comprises dsDNA that has been broken at both strands. In a further embodiment, the receptor is composed of an anti-tubulin antibody and the target molecular material is composed of tubulin. In an even further embodiment, the receptor is composed of an Anti-p53 antibody and the target molecular material is composed of p53 or p53 mutants. In one embodiment when the probe is composed of a carbon nano-fiber, the receptor comprises poly T oligo, and the target molecular material is at least one polyadenylated mRNA.

In another aspect of the present invention, the method of extracting molecular material includes a probe having a tether, in which the tether may be manipulated in response to the application of a voltage potential. In one embodiment, the method includes:
providing a probe comprising a penetration portion comprising a nanoscale surface for penetrating a biological compartment, the penetration portion including a cavity and a tether, the tether including a receptor having an affinity for a target molecular material, wherein the tether has a charged surface of a first type charge;
inserting at least the penetrating portion of the probe into the biological compartment;
applying a first potential to the probe to produce a substantially same type charge as the first type charge of the charged surface of the tether, wherein at least a portion of the tether extends to an exterior of the cavity, wherein the receptor engages the target molecular material;
applying a second potential to the probe to produce a substantially opposing charge as the first type charge of the charged surface of the tether, wherein at least a portion of the tether and the target molecular material engaged to the receptor retract within the cavity; and
extracting the probe and the target molecular material engaged to the receptor of the probe from the biological compartment.

In one embodiment, the method further includes applying a potential to the probe to retract the tether within the cavity prior to inserting the penetrating portion of the probe into the biological compartment, wherein the potential applied to the probe produces a charge opposite the charged surface of the tether. In one embodiment, the tether is composed of a linear chain molecule or a linear molecular array. In one embodiment, the tether further includes a nuclear targeting signal. In one embodiment, the receptor is reversibly connected to the penetrating portion of the probe by a cleavable linkage group, wherein the cleavable linkage group may be provided by a disulfide bond.

In another aspect of the invention, a probe is provided that may extract a molecular species from a biological compartment, wherein the probe includes a tether for engaging molecular material. In one embodiment, the inventive probe includes:
a carbon nano-fiber;
a dielectric cylinder present on the carbon nano-fiber, the dielectric cylinder having an opening extending to a surface of the carbon nano-fiber that defines a cavity; and
a tether comprising a receptor, the tether connected to the surface of the carbon nano-fiber.

In one embodiment, the dielectric cylinder is present on an end of the carbon nano-fiber that provides the penetrating portion of the probe. In one embodiment, the dielectric cylinder provides a cavity, in which the sidewalls of the cavity are defined by the dielectric cylinder and the base of the cavity is provided by a surface of the carbon nano-fiber.

In one embodiment, the dielectric cylinder has a radial dimension of less than about 300 nm, and the length of the probe is less than about 100 microns.

In one embodiment, the tether provides that the receptor be manipulated within the cell to capture the target molecular material. In one embodiment, a first end of the tether is connected to the surface (also referred to as a recessed surface) of the carbon nano-fiber within the cavity. In one embodiment, the receptor is positioned at an end of the tether that is opposite the end of the tether that is connected to the surface of the carbon nano-fiber, wherein the receptor may be extended from and retracted into the cavity formed by the dielectric cylinder. In another embodiment, the receptor is positioned along an entire length of the tether.

In one embodiment, the tether may be a linear chain molecule. In one embodiment, the linear chain molecule may be a single chain molecule, or may be an array of single chain molecules. In one embodiment, the linear chain molecule may include DNA, RNA, protein chains or combinations thereof. In one embodiment, the linear chain molecule is composed of a peptide nucleic acid (PNA) including a chemical backbone of N-(2-aminoethyl)-glycine units linked by peptide bonds and bases linked to the backbone by methylene carbonyl bonds, wherein the bases include purine, pyrimidine or combinations thereof. In another embodiment, the linear chain molecule may include an amine bonded through carboxyl groups to the surface of the carbon nano-fiber.

In one embodiment, the tether is reversibly connected to the surface of the carbon nano-fiber by a cleavable linkage group. A disulfide bond is one example of a cleavable linkage group, wherein the disulfide bond is cleaved by application of a reducing agent (i.e. Dithiolthreitol, DTT) or by application of a reducing potential.

In one embodiment, the tether has a charged surface of a first type charge, e.g. a negative charge, wherein applying a potential to the carbon nano-fiber to produce a substantially same type charge, e.g., a negative charge, as the charged surface of the tether positions a portion of the tether to an exterior of the cavity, and applying a potential to the carbon nano-fiber to produce an opposing type charge, e.g., positive charge, to the charged surface of the tether positions the tether within the cavity.

In one embodiment, the receptor includes a composition selected for engaging a target molecular material. In one embodiment, the receptors can be DNA, proteins, RNA, or peptide nucleic acids. In one embodiment, in which the receptor is composed of DNA, proteins, RNA, or peptide nucleic acids, the receptor may be connected to the tether by covalent bonding.

In one embodiment, the receptor includes an amine site for engagement to carboxyl acid sites. In another embodiment, the receptors may be crosslinked to a carbon surface, such as the base of the cavity that is provided by the carbon nano-fiber and the dielectric cylinder. In a further embodiment, the receptors may be connected to the surface of the carbon nano-fiber by covalent bonds, e.g. amine-carboxy condensation to amide, or by affinity forces, e.g., biotin-streptavidin. In yet another embodiment, the attachment of the receptor is provided by an organosilane composition.

BRIEF DESCRIPTION OF THE DRAWINGS

The following detailed description, given by way of example and not intended to limit the invention solely thereto, will best be appreciated in conjunction with the accompanying drawings, wherein like reference numerals denote like elements and parts, in which.

DETAILED DESCRIPTION OF THE INVENTION

Figure 1A:
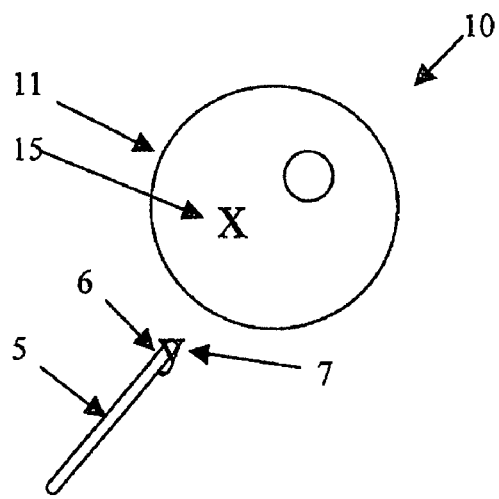
FIGS. 1A-1C depict side cross sectional views of one embodiment of a method for extracting molecular material from a cell, in accordance with the present invention.

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

The embodiments of the present invention relate to novel methods and structures for extracting molecular material from biological compartments. When describing the methods, the following terms have the following meanings, unless otherwise indicated.

As used herein, the term "nanoscale surface" denotes a surface of the probe, particularly the surface of the penetrating portion of the probe, in which the greatest dimension of that surface is less than 1 micron.

As used herein, the term "biological compartment" is defined by the space contained within a membrane of a single cell or by the space between adjacent cells of a tissue.

As used throughout the present disclosure, the term "receptor" denotes a biological molecule that is disposed on the portion of a probe that selectively receives a targeted molecular material.

The term "biological molecule" as used throughout the present disclosure includes poly nucleic acids, poly amino acids, carbohydrates, lipids, or peptide nucleic acids (PNAs). Examples of poly nucleic acids include, but are not limited to: DNA and RNA. Examples of poly amino acids include, but are not limited to: peptides, polypeptides, and proteins. Examples of carbohydrates include, but are not limited to monosaccharides, disaccharides, and polysaccharides. Lipids may include, but are not limited to: triglycerides, steroids, and phospholipids. PNAs refer to nucleic acids having a peptide-bond backbone.

As used herein, the term "amine" denotes organic compounds and a type of functional group that contain nitrogen. Amines structurally resemble ammonia, wherein one or more hydrogen atoms are replaced by organic substituents, such as alkyl and aryl groups.

As used herein, "organosilane" means an organic compound in which silicon is bonded to silicon dioxide coating a carbon nano-structure, e.g., carbon nano-fiber or nano-tube.

The term "cleavable linkage" denotes a linkage group that may be chemically, electrochemically, or optically cleaved.

The term "charged surface" denotes an ionically charged surface that is electrically positive or negative.

As used herein, the term "hydrophobic" means a material that repels water by surface tension.

As used herein, the terms "insulating" or "insulating properties" denotes a material having a room temperature conductivity of less than about $10^{-10}(\Omega\text{-m})^{-1}$.

As used herein, a "dielectric" is a non-metallic solid displaying insulating properties.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

For purposes of the description hereinafter, the terms "upper", "lower", "right", "left", "vertical", "horizontal", "top", "bottom", and derivatives thereof shall relate to the invention, as it is oriented in the drawing figures.

The present invention provides a method of extracting molecular material by an affinity-based extraction from a biological compartment. In contrast to traditional extraction from cell lysate, the present invention may extract molecular material while maintaining cell viability, hence providing that a molecular material, for example, protein, is captured in its native context, i.e., not after suffering alterations due to lysis and non-intracellular residence. In one embodiment, the present invention allows for a probed cell to be re-sampled in response to an extraction result. For example, in the instance where one cell out of 800,000 is found positive for a particular protein, that one cell can be individually selected and cloned.

Figure 1B:
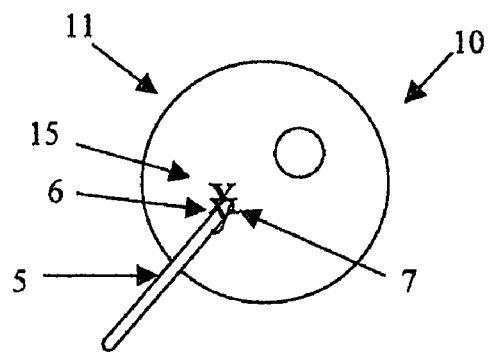
Figure 1C:
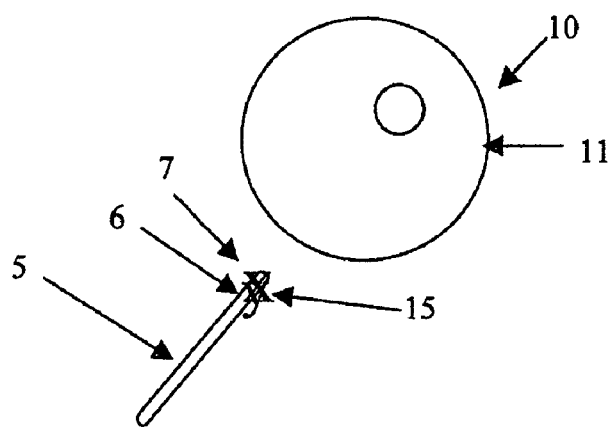

FIGS. 1A-1C depict one embodiment of a method for extracting molecular material 15 from a cell 10. In one embodiment, the cell 10 may have a dimension of 10 microns or less. In another embodiment, the cell 10 may have a dimension ranging from about 500 nm to about 100 microns. In one embodiment, the cell may be a mammalian cell 10. In another embodiment, the cell may be a prokaryotic or eukaryotic cell. In another embodiment, the cell may have a greatest dimension of 100 micron or less. Although FIGS. 1A-1C depict molecular extraction from a cell 10, it is noted that the present application is equally applicable to any biological compartment. For example, in one embodiment, the method and structures of the present invention may be utilized to extract molecular material from a single cell of a tissue. In another embodiment, the method and structures of the present invention may be used to extract molecular material from the intercellular space between at least two cells in a tissue. A tissue is an aggregation of similar cells and associated intercellular matter acting together to perform one or more functions. For example, the method and structures of the present invention may be used to extract material from tissue of a biopsied tumor, or from the peripheral tissue surrounding where a biopsied tumor was surgically removed. In another example, the probe 5 of the present invention can be used to extract molecular material 15 from a tissue with suspected malignancy. In an even further example, the probe 5 can be used to extract molecular material from the skin of nude mice. In yet a further example, the probe 5 can be used to extract material from internal organ tissue during invasive surgery, or from tissues of the eyes, ears, nose, throat, or intestinal linings with minimal invasiveness.

Referring to FIG. 1A, in one embodiment, the method for extracting molecular material 15 is performed with a probe 5 having a penetration portion 6 with a nanoscale surface and a receptor 7 that is present on the penetrating portion 6 of the probe 5, wherein the receptor 7 having an affinity for a target molecular material 15. The target molecular material 15 may be any intracellular molecule and may include nucleic acids (DNA or RNA) and proteins (e.g., enzymes, antibodies, etc.). In one embodiment, the target molecular material is obtained or derived from a cell infected with a cellular pathogen. Examples of cellular pathogens include viruses, parasites and bacteria. In one embodiment, the molecular material 15 that is extracted from the biological compartment using the probe and method of the present invention is polynucleic acids and polyamino acids.

In one embodiment, the probe 5 is provided by a structure having dimensions that are selected to penetrate the cell 10 without substantially effecting cell viability. In particular, the probe 5 has radial dimensions small enough to penetrate within the cells 10 and is long enough to provide significant penetration depth into the cell's sub-cellular regions. In one embodiment, the probe 5 is cylindrical in morphology or conical, wherein the conicity of the structure provides mechanical robustness while providing a nanoscale tip that minimizes cell damage during penetration, residence, and removal of the molecular material from the cell.

In one embodiment, at least the penetrating portion 6 of the probe 5 has a radial dimension of less than about 300 nm. In another embodiment, at least the penetrating portion 6 of the probe 5 has a radial dimension of less than about 100 nm. In an even further embodiment, the probe 5 has a radial dimension of less then about 50 nm. In one embodiment when the probe 5 is extracting molecular material from mammalian cells, at least the penetrating portion of the probe 5 has a radial dimension of about 300 nm or less. In another embodiment when the probe 5 is extracting molecular material from prokaryotic cells, at least the penetrating portion of the probe 5 has a radial dimension of about 100 nm or less. The radial dimension is the greatest width W1 of the penetrating portion 6 of the probe 5. In one embodiment when the probe 5 has a circular cross section, the radial dimension is the diameter of the penetrating portion 6 of the probe 5.

In one embodiment, the probe 5 has a length $L_1$ of less than about 100 microns. In another embodiment, the probe 5 has a length $L_1$ ranging from about 1 micron to about 80 microns. In an even further embodiment, the probe 5 has a length $L_1$ of less than 10 microns.

In one embodiment when the molecular material 15 is being extracted from a mammalian cell, the radial dimension of the penetrating portion 6 is less than about 300 nm, and the length $L_1$ of the probe 5 ranges from about 1 micron to about 20 microns. In another embodiment, when the molecular material 15 is being extracted from a tissue, such as a suspected malignancy of the ear, nose, or throat, the radial dimension of the penetrating portion 6 is less than about 300 nm, and the length $L_1$ of the probe 5 ranges from about 1 micron to about 80 microns. In a further embodiment when a molecular material 15 is being extracted from a prokaryotic cell, the radial dimension of the penetrating portion 6 of the probe 5 is less than about 100 nm, and the length $L_1$ of the probe 5 ranges from about 1 micron to about 5 microns. The radial dimension and length of the probe 5 can be determined based on the size of the biological compartment, e.g., cell, that the molecular material is being extracted from.

Embodiments of probes 5 that may be used in accordance with the present invention include needles, spikes, pipes, partial pipes, nano-fibers, and nano-tubes of nanoscale dimensions. In one embodiment, the probe 5 is constructed of carbon nano-fibers. A carbon nano-fiber is a cylindrical nanostructure with at least one graphene layer arranged as stacked cones, cups or plates. Graphene is a one atom thick sheet of graphite. In another embodiment, the probe 5 is constructed of carbon nano-tubes. A carbon nano-tube is at least one graphene layer wrapped into a cylinder. A single wall carbon nano-tube is a graphene rolled up into a seamless cylinder with diameter of the order of a nanometer. In an even further embodiment, the probe 5 is constructed of a silicon dioxide nano-tube, wherein the silicon dioxide nano-tube may be formed by providing a carbon nano-fiber core, oxidizing the carbon nano-fiber core, and then removing the carbon nano-fiber core by an etch process selective to removing the carbon nano-fiber core, wherein the oxide remains to provide the tube geometry.

In another embodiment, the probe 5 includes an array of the aforementioned structures, wherein the array may be a vertically aligned array, such as a vertically aligned array of carbon nano-fibers, carbon nano-tubes, or silicon dioxide nano-tubes. A vertically aligned carbon nano-fiber is a carbon nano-fiber having an arrangement with the major axis of the carbon nano-fiber is aligned with other carbon nano-fibers oriented on an underlying substrate surface. In one embodiment, a vertically aligned carbon nano-fiber is a nano-fiber that has been synthesized at an angle to the underlying substrate that ranges from approximately 20 degrees to approximately 90 degrees (perpendicular).

In one embodiment, vertically aligned carbon nano-fibers (VACNF) may be synthesized singularly or in ordered arrays with control of the shape, length, diameter, orientation, position, and surface chemistry of the nano-fibers. In one embodiment, carbon nano-fibers may be chemically modified and inserted into cells 10 without significantly effecting cellular viability. VACNF arrays can penetrate a diverse array of cell types, including, but not limited to: mammalian cells, plant cells, yeast cells, and grass pollen. In another embodiment, the probes 5 are be provided by carbon nano-tubes.

In another embodiment, the probe 5 is constructed of a nano-tube composed of silicon dioxide. In one embodiment, a nano-tube of silicon dioxide is formed by providing a carbon nano-fiber; forming an oxide coating on the exterior surface of the carbon nano-fiber; and removing the carbon nano-fiber, in which the oxide coating remains to provide the nano-tube. In one embodiment, forming the oxide coating includes chemical vapor deposition. In one embodiment, the removal of the carbon nano-fiber following oxide coating formation is provided by an etch process, such as reactive ion etch, that removes carbon selective to oxide.

In a further embodiment, the probe 5 is constructed of a partial nano-tube that may include a carbon nano-fiber core and a dielectric cylinder, such as a silicon dioxide cylinder, wherein the dielectric cylinder is positioned on at least the penetrating portion 6 of the probe 5. In one embodiment, a surface of the carbon nano-fiber core is recessed within the dielectric cylinder to provide a cavity having an opening present at the face of the penetrating portion 6 of the probe 5, wherein the base of the cavity is provided by the recessed surface of the carbon nano-fiber core. In one embodiment, a partial nano-tube composed of a carbon nano-fiber core and dielectric cylinder is formed by a method that includes the steps of providing a carbon nano-fiber core; forming an oxide coating on the exterior surface of the carbon nano-fiber core to provide the dielectric cylinder; and recessing a surface of the carbon nano-fiber core to provide the cavity. In one embodiment, forming the oxide coating includes chemical vapor deposition. In one embodiment, the recessing of the carbon nano-fiber following the formation of the dielectric cylinder is provided by a timed etch process, such as reactive ion etch, that removes carbon selective to oxide. In one embodiment, the recessed surface of the carbon nano-fiber is separated from the surface of the dielectric cylinder that first contacts the biological tissue during extraction of the targeted molecular material by a dimension ranging from about 100 nm to about 5 microns. In one embodiment, the cavity provides a sequestered environment that reduces shear during insertion and extraction of the probe 5 into the biological tissue, e.g., cell 10. Shear forces include forces that the tether, and molecular material that is engaged to the tether, are subjected to during penetration of the probe into the cell and extraction of the probe from the cell, wherein the forces are at least due in part to the fluid viscosity and molecular interactions of the cell.

In another embodiment, the probe 5 is provided by micromachined needles. For example, in one embodiment, micromachined needles are formed of silica and are formed by an extrusion process. In another embodiment the micromachined needles are manufacturing using a process that includes an etch process. In yet another embodiment, they are formed by a thermal drawing process.

In yet an even further embodiment, the probe 5 may include a hydrophobic coating. The hydrophobic coating may modify the probe 5 to inhibit cellular attachment. In one embodiment when the probe 5 is utilized to extract molecular material 15 from cells 10, the coating, i.e., the hydrophobic coating, may facilitate penetration of the probe 5 through the cell membrane 11 without attachment of cell membrane 11 to the probe 5. In one embodiment, the hydrophobic coating may include parylene and/or spun photoresist that is used to coat at least a portion of the probe 5. In another embodiment when the probe 5 is composed of a carbon containing nano-structure, such as a carbon nano-tube, carbon nano-fiber, or partial tube including an exposed surface of a carbon nano-fiber core, the hydrophobic coating is provided by any molecular species that hydrophobically reacts with the benzene surface of the carbon containing nanostructure to produce a functional handle, such as tyramine, wherein the functional handle provides a reactive site for further chemical modification of the coating.

FIG. 1B depicts one embodiment of inserting the probe 5 through a membrane 11 of a biological compartment, e.g., cell 10, where a receptor 7 present on the penetrating portion 6 of the probe 5 engages the target molecular material 15. In one embodiment, a surface of at least the penetrant portion 6 of the probe 5, or at least a portion of the surface of the penetrant portion 6 of the probe 5, is functionalized with a specific receptor or affinity site (hereafter referred to as a receptor 7) for engagement to the target molecular material 15 to be extracted.

In one embodiment, the penetrating surface 6 of the probe 5 is functionalized using a wide array of chemistries to provide the receptor 7. For example, in one embodiment when the probe 5 is composed of a carbon containing nanostructure, such as carbon nano-fiber or carbon nano-tube, the attachment chemistries may include but are not limited to EDC-mediated (1-ethyl-3-(3-dimethylaminopropyl)carbodiimide) condensation reaction (hereafter referred to as EDC condensation) of primary amines on molecules to be attached to carboxylic acid sites to the carbon surface of the probe 5; entrapment of receptors 7 in electropolymerized or polymerized polymer films to the carbon surface of the probe 5, UV crosslinking receptors 7 to the carbon surface of the probe 5, or crosslinking to the carbon surface of the probe 5 via cross linking agents, such as gluteraldehyde.

In another embodiment when the probe 5 is composed of a silicon dioxide, such as silicon dioxide nano-tubes and silicon dioxide partial nano-tubes, the probe 5 is functionalized with a variety of organosilane chemistries to provide subsequent attachment of the receptor 7.

In a further embodiment, in which the probe 5 is provided by a nano-pipe and/or partial nano-pipe construction, the nano-pipe or partial nano-pipe is functionalized to provide a receptor 7 on at least a portion of an inner surface and/or outer surface of the penetrating portion 6 of the probe 5. For example, a carbon nano-fiber core positioned within a cavity provided by a dielectric cylinder composed of an oxide sheath in a partial nano-pipe construction is functionalized with a receptor 7, while the oxide sheath of the dielectric cylinder may not be functionalized with receptors 7. As such, ligand receptor interaction occurs within the cavity provided by the dielectric cylinder of the partial pipe construction, and extraction does not result in shear of extracted molecular material due to the protection that is provided by the oxide sheath of the dielectric cylinder during extraction.

In one embodiment, functionalization may include the direct immobilization of receptors 7, the embedding of receptors 7 in surface coating films, or the decoration of the surface of the probe 5 with tethers that in turn are functionalized with at least one receptor 7. For example, dendrites could be used to tether a large number of receptors 7 to the penetrating portion 6 of the probe 5.

In one embodiment, the penetrating portion 6 of the probe 5 may provide a localization signal so that the receptor 7 is directed to a sub-cellular location. For example, nuclear localization signals (NLS) are amino acid sequences that provide for cellular trafficking of the material to the nucleus. In one embodiment, the NLS sequence PKKKRKV (SEQ ID NO:1), from the SV40 large T antigen, is used to provide nuclear localization.

In another embodiment, once the probe 5 is inserted into the cell, the receptor 7 engages the targeted molecular material 15 by an affinity type attraction. Generally, affinity refers to the binding interaction between molecules, for example, DNA-protein, e.g., promoter-transcription factor, protein-protein, protein-RNA. Affinity interactions may be provided by nucleotide/nucleotide base pairing, intercalation, ionic interactions, protein-protein docking, protein-DNA docking, protein RNA docking, and sequence specific interactions.

FIG. 1C depicts extracting the probe 5 and the target molecular material 15 that is engaged to the inserting portion 6 of the probe 5 from the biological tissue, e.g. cell 10, in accordance with one embodiment of the present invention. In one embodiment, following extraction of the molecular material 15 from the cell 10, an elution chemistry is used to release the molecular material 15 from the receptor 7. An elution chemistry removes an antibody from the antigen to which it is attached and is typically a solvent or a competing species of the affinity interaction. In another embodiment, a cleavable linkage group is present between the receptor 7 and the penetrating portion 6 of the probe 5, wherein following extraction the cleavable linkage group is broken to separate the target molecular material 15 from the probe 5. In one embodiment, the cleavable linkage group is provided by a disulfide bond. In one embodiment, the cleavable linkage group is cleaved chemically, electrochemically or optically. For example, the cleavable linkage group is separated by the application of a reducing agent, e.g., dithiolthreitol, DTT, or a reducing potential.

FIGS. 2A-2E depict another embodiment of the present invention in which the target molecular material 15 is extracted from a viable cell 10 with a probe 5 that includes a tether 20, wherein the tether 20 provides for flexibility within the cell 10 so that a receptor 7 may be translated into engagement with the target molecular material 15. In this embodiment, the probe 5 is composed of at least one nano-fiber that provides rigidity and strength during the penetration of the probe 5 through the cell membrane 11, and the flexible tethers 20 provides translation within the cell 10 for a more effective capture of the target molecular material 15. In one embodiment, electrically repulsive and attractive forces may manipulate the tether 20.

Figure 2A:
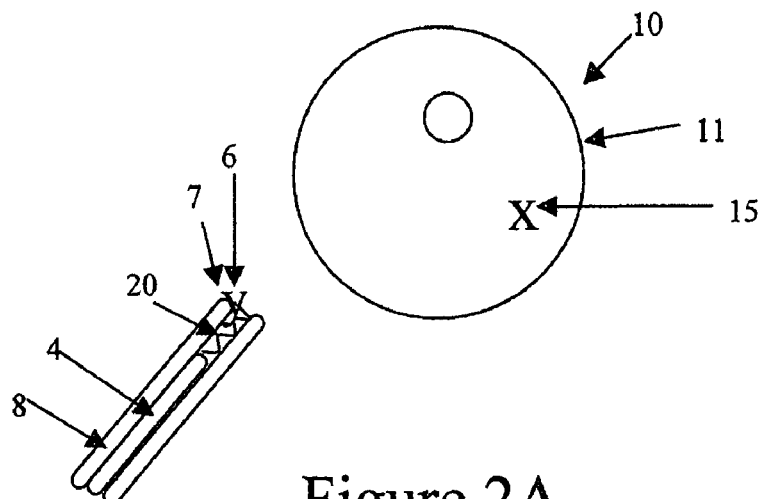
FIGS. 2A-2E depict side cross sectional views of another method for extracting molecular material from a cell, in accordance with the present invention.

FIG. 2A depicts one embodiment of a probe 5 and tether 20 prior to insertion of the probe 5 into the cell 10. In this embodiment, the probe 5 is provided by a partial nano-tube. More specifically, the partial nano-tube construction of the probe 5 may include a carbon nano-fiber core 4 and a dielectric cylinder 8. In one embodiment, the dielectric cylinder 8 is present on the exterior surface of the carbon nano-fiber core 4. In one embodiment, the dielectric cylinder 8 is an oxide, such as silicon dioxide.

In one embodiment, the probe 5 includes a cavity 9 that is present at the penetrating portion 6 of the probe 5. The cavity 9 is provided by recessing the carbon nano-fiber core 4 within the dielectric cylinder 8. In one embodiment, the cavity 9 provided by the dielectric cylinder 8 may have a width ranging from about 50 nm to about 500 nm. In one embodiment, the base of the cavity 9 is provided by the recessed surface of the carbon nano-fiber core 4.

In one embodiment when the target molecular material 15 is being removed from the cell 10, the width $W_2$ of the dielectric cylinder 8 that is present on at least the penetrating portion 6 of the probe 5 is less than about 300 nm, and the length $L_2$ of the probe 5 may range from about 1 micron to about 10 microns. In a further embodiment when the molecular material 15 is being extracted from prokaryotes, the width $W_2$ of the penetrating portion 6 of the probe 5 is less than 100 nm, and the length $L_2$ of the probe 5 may range from about 1 micron to about 5 microns.

Still referring to FIG. 2A, a tether 20 including at least one receptor 7 having an affinity for the target molecular material 15 is provided in attachment with the probe 5. In one embodiment, the tether 20 has a length ranging from about 100 Å to about 1 micron. In another embodiment, the tether 20 has a length ranging from about 100 Å to about 500 nm.

In one embodiment, the tether 20 is composed of a linear chain molecule or is composed of a linear molecular array. One example of a linear chain molecule that is suitable for a tether 20 in accordance with the present invention includes a nucleotide sequence of poly(dA) or poly(dT). Further examples of compositions and molecules that may provide the tether 20 in accordance with the present invention include, but are not limited to: polyamino acid, poly-D-lysine, poly-L-lysine, poly-D-glutamic acid, poly-L-glutamic acid or combinations thereof. In one embodiment, the linear chain molecule of the tether 20 may include DNA or PNA (peptide nucleic acids), or may include arrays of linear dendrimers. Examples of liner dendrimers include, but are not limited to: polyethylenimine and branched polyethylenimine.

In one embodiment, in which the tether 20 is DNA, the DNA is end-tethered to the recessed surface of the carbon nano-fiber core 4 that is positioned within the cavity 9 defined by the dielectric cylinder 8. In one embodiment, when the linear chain molecule that provides the tether 20 is DNA, the DNA is a single strand or a double stranded molecule. In one embodiment, in which the tether 20 is a DNA molecule, the length of the tether 20 ranges from about 100 Å to about 1 micron. In another embodiment, in which the tether 20 is a DNA molecule, the length of the tether 20 ranges from about 100 Å to about 500 nm. In an even further embodiment, in which the tether 20 is a DNA molecule, the length of the tether 20 ranges from about 100 Å to about 5 microns.

In one embodiment, the DNA tether 20 can be end-tethered to the recessed surface of the carbon nano-fiber core 4 within the cavity 9 by an EDC-mediated (1-ethyl-3-(3-dimethylaminopropyl) carbodiimide) condensation reaction (hereafter referred to as EDC condensation) of a terminal amine from a sticky end guanine. More specifically, in one embodiment, end tethering of the DNA tether 20 can be provided by direct condensation of base amines (guanine) to COOH groups on the recessed surface of the carbon nano-fiber core 4 of the probe 5 by EDC condensation.

In another embodiment, the tether 20 is provided by oligos, such as synthetic oligos, that can be connected, e.g. end tethered, to the recessed surface of the carbon nano-fiber core 4 using a variety of strategies. For example, biotinylated oligos are attached to the recessed surface of the carbon nano-fiber core 4 within the cavity 9 by biotin end label engagement to streptavidin coated carbon nano-fiber core, wherein streptavidin is either dried or electrochemically polymerized to the carbon nanofiber fiber core 4. In one embodiment, the streptavidin is coated to the carbon nano-fiber core 4 using UV crosslinking or EDC condensation. In one embodiment, the oligos may be ligated to a longer DNA tether. In one embodiment, the tether 20 composed of oligos has a length ranging from about 100 Å to about 1 micron. In another embodiment, the tether 20 composed of oligos has a length ranging from about 100 Å to about 500 nm. In an even further embodiment, the tether 20 composed of oligos has a length ranging from about 100 Å to about 5 microns.

In one embodiment, the tether 20 is modified to feature receptor site(s) 7 on its ends, on a portion of the tether's 20 length, or along the tether's entire length. For example, in one embodiment, a tether 20 composed of DNA is biotinylated with psoralen-biotin through psoralen intercalation and UV crosslinking, wherein the biotin is used as a handle for any avidin modified receptor. In another embodiment, a biotinylated tether 20 is used to capture streptavidin, which in turn captures more biotinylated receptors, since streptavidin features 4 biotin capture sites. Other examples of receptors include, but are not limited to: antibodies to antigens and/or proteins and proteins for capture of antibodies, DNA for capture of DNA binding proteins/transcription factors/polymerases and DNA binding proteins for capture of specific DNA, RNA for capture of RNA specific binding proteins including RNA dependent RNA polymerase and vice versa, mRNA for capture of mRNA binding materials, such as enzymes for post transcriptional splicing and polyadenylation (and vice versa), polyT oligonucleotides for capture of nonspecific polyadenylated mRNA, oligonucleotide sequences for capture of mRNAs, modified nucleic acids for improved stability and reduced degradation, such as peptide nucleic acids or methylated nucleic acids, antibodies to viral ligands, and phage displayed motifs.

In yet another embodiment, the tether 20 itself may provide the receptor site 7. In one example, a tether 20 composed of DNA could be used to engage operators that bind to promoter sites on the tether 20. For example, a tether 20 composed of DNA may provide a receptor 7 for transcription factors, polymerases, topoisomerases, and other DNA binding species.

Still referring to FIG. 2A, in one embodiment, prior to cell penetration, the tether 20 can be retracted into the cavity 9 at the penetrating portion 6 of the probe 5. The movement of the tether 20 is controlled by migration if the linear tether 20 is charged, such as having a surface charge. In one embodiment, a tether 20 connected at a first end to the recessed surface of the carbon nano-fiber core 4 and having a charged surface of a first type, such as a negatively charged surface, is retracted into the cavity 20 by producing an opposing charge, such as a positive charge, to the end of the carbon nano-fiber core 4 opposite the end to which the tether 20 is attached. In one embodiment, the tether 20 connected at a first end to the recessed surface of the carbon nano-fiber core 4 and having a charged surface of a first type, such as a negatively charged surface, is extended to the exterior of the cavity 20 by producing a substantially same charge, such as a negative charge, to end of the carbon nano-fiber core 4 opposite the end to which the tether 20 is attached.

More specifically, in one embodiment in which the tether 20 is composed of linear anionic DNA, the tether 20 is accumulated within the cavity 9 by applying a positive bias to the carbon nano-fiber core 4 with respect to an external reference electrode. In one embodiment, a potential voltage is applied to the carbon nano-fiber core 4 to retract the tether 20 within the cavity 9 prior to inserting the penetrating portion 6 of the probe 5 through the membrane 11 of the cell 10, wherein the voltage potential applied to the probe 5 produces a charge opposite the charged surface of the tether 20.

Figure 2B:
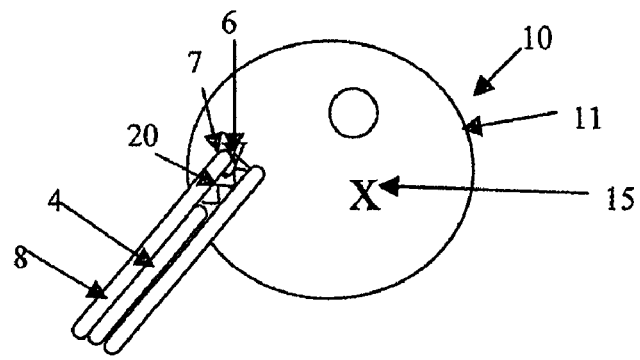

FIG. 2B depicts inserting at least the penetrating portion 6 of the probe 5 through the membrane 11 of a cell 10. In one embodiment, the tether 20 is maintained within the cavity 9 during cellular penetration by maintaining the voltage gradient within the cavity 9. In another embodiment, the tether 20 is maintained within the cavity 9 by immobilizing the tether 20 within the pipe with a dissolvable or digestible plug (not shown). For example, in one embodiment, an electrokinetically captured protein may contain the tether 20 by plugging the cavity 9 during insertion of the probe 5 through the cell membrane 11, wherein the plug is digested by intracellular enzymes once positioned within the cell 10 to release the tether 20.

Figure 2C:
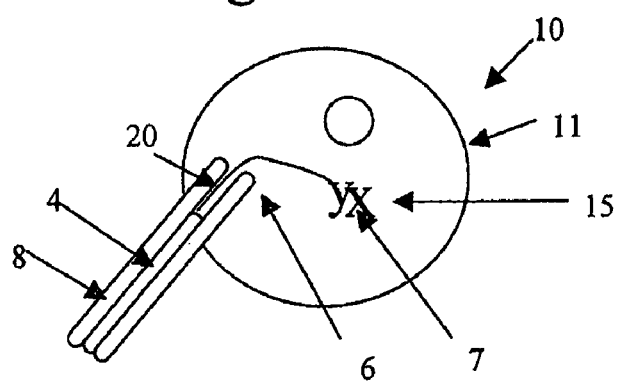

FIG. 2C depicts applying a first voltage potential to the probe 5 to produce a substantially same type charge, e.g., negative charge, as the charged surface of the tether 20, e.g., negative charge, to extend the tether 20 to an exterior of the cavity 9 and into the cell 10, wherein the receptor 7 engages the target molecular material 15. Voltage potentials are applied to the carbon nano-fiber core 4 by addressing the carbon nano-fiber core 4 through electrical contact to an electrically conductive substrate. In one embodiment, the electrically conductive substrate may be composed of a metal or composed of a semiconducting material having an electrically conductive coating. In one embodiment when the electrically conductive substrate is composed of a semiconducting material, the substrate is a silicon containing substrate having a coated material stack of TiW and TiSi. In one embodiment when the electrically conductive substrate is composed of a metal, the substrate may include W, Ti, Cu, Au, or combinations thereof. In one embodiment, the electrical contact between the electrically conductive substrate and the carbon nano-fiber core is provided by growth of the carbon nano-fiber onto the electrically conductive substrate or subsequent to growth of the carbon nano-fiber.

In one embodiment, tether 20 of the probe 5 may provide a localization signal so that the receptor 7 is directed to a sub-cellular location. For example, in one embodiment when the tether 20 is composed of DNA, the end of the DNA tether 20 is modified with a variety of peptide based nuclear targeting signals, which may include VP1 protein from simian virus 40, M1 from influenza virus, the T antigen from SV40, or combinations thereof. In another embodiment, portions of targeting amino acid sequences may also be used, such as APTKRK (SEQ ID NO:2) from SV40 VP1, RKLKR (SEQ ID NO:3) from Influenza M1, and PKKKRKV (SEQ ID NO:1) from a Large T antigen of SV40. In one embodiment, the receptor 7 is strung behind the targeting sequence of a linear molecule tether 20, such as DNA. Following capture of the target molecular material 15, the tether 15 and its captured target molecular material 15 is retracted within the cavity 9 by the application of potential and electrophoretic migration of the tether 20.

Figure 2D:
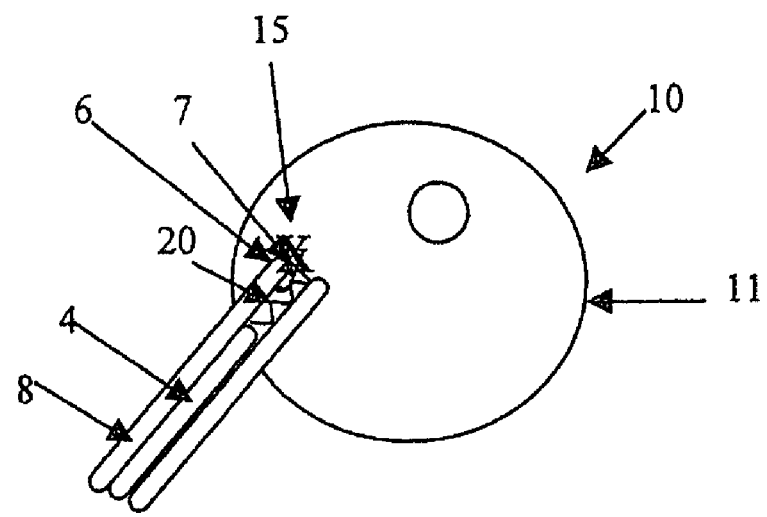

FIG. 2D depicts one embodiment of applying a second voltage potential to the probe 5 to produce a substantially opposing charge, e.g., positive charge, as the charged surface, e.g., negative charge, of the tether 20 to retract the tether 20 and the target molecular material 15 that has engaged to the receptor 7 within the cavity 9. By containing the target molecular material 15 within the cavity 9, the tether 20 and the captured target molecular material 15 are protected from shear forces during extraction.

Figure 2E:
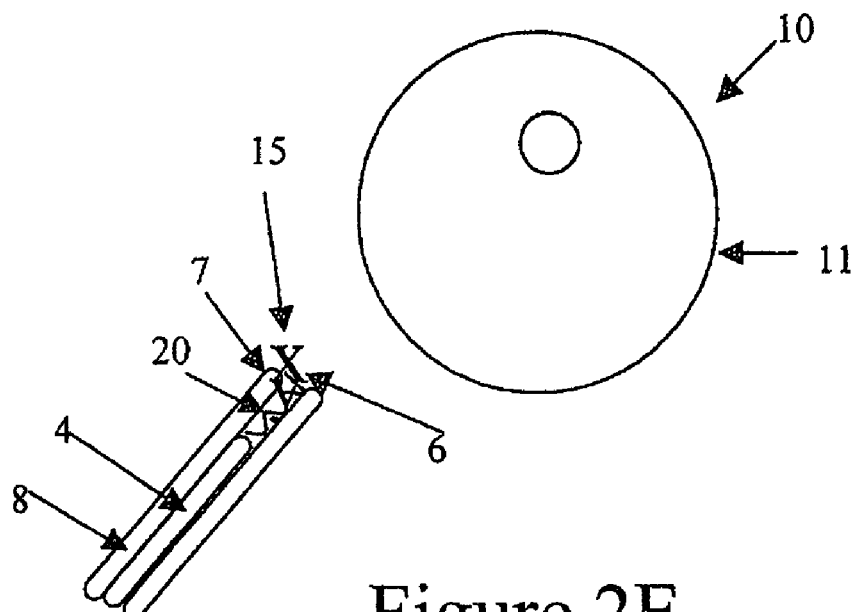

FIG. 2E depicts extracting the probe 5 and the target molecular material 15 engaged to the receptor 7 of the tether 20 from the cell 10. In one embodiment, the probe 5 may feature spatial registration such that the results of the extraction can be directed correlated to specific locations within the sampled tissue or cells 10, thus enabling resampling or selection of specific cells or regions of tissue for further analysis or isolated propagation.

In one embodiment, following extraction, the target molecular material 15 can be analyzed. In one embodiment, a fluorescent antibody can be washed over a apparatus including the probes of the present invention, wherein the fluorescent antibody binds to a target protein and provides a visual marker of where the protein is present on the apparatus. In another embodiment, complementary mRNA to a tethered oligonucleotide sequence is visualized by an intercalating dye, such as picogreen or propidium iodide. In another embodiment when a polyT tethered sequence is used to capture mRNA via the polyA tag, a complimentary sequence to a specific portion of the captured mRNA is washed over the apparatus following extraction and resultant hybridization is visualized by an intercalating dye. In a further embodiment, the complimentary sequence to a specific mRNA may be dye labeled itself to indicate presence of the target molecular material 15 on an extraction array, wherein the extraction array includes one or more of the probes 5.

In another embodiment, the captured target molecular material 15 is eluted from the receptor 7 and analyzed. For example, polyA tagged mRNA captured with a polyT tag can be eluted by elevating the temperature of the system above the denaturation temperature of the polyA/polyT complementation (i.e. 96 deg C. maximum). In another embodiment, chaotropic agents can be used for elution. In a further embodiment when the target molecular material 15 includes an antibody and the receptor 7 is composed of antigens, elution is achieved with acidic agents, such as acetic acid. In an even further embodiment, the target molecular material 15 can be locally eluted and local regions can be analyzed for presence of the target protein. For example, a microfluidic system could be used to elute the target molecular material 15 from localized regions of the extraction apparatus and this local elute could be sampled in a mass spectrometer. Local regions of the extraction apparatus could also be laser ablated locally to provide a scanning input of the platform surface into a mass spectrometer.

The above elution strategies are equally applicable to the embodiments described above with reference to FIGS. 1A-1C and FIGS. 2A-2E.

Figure 3:
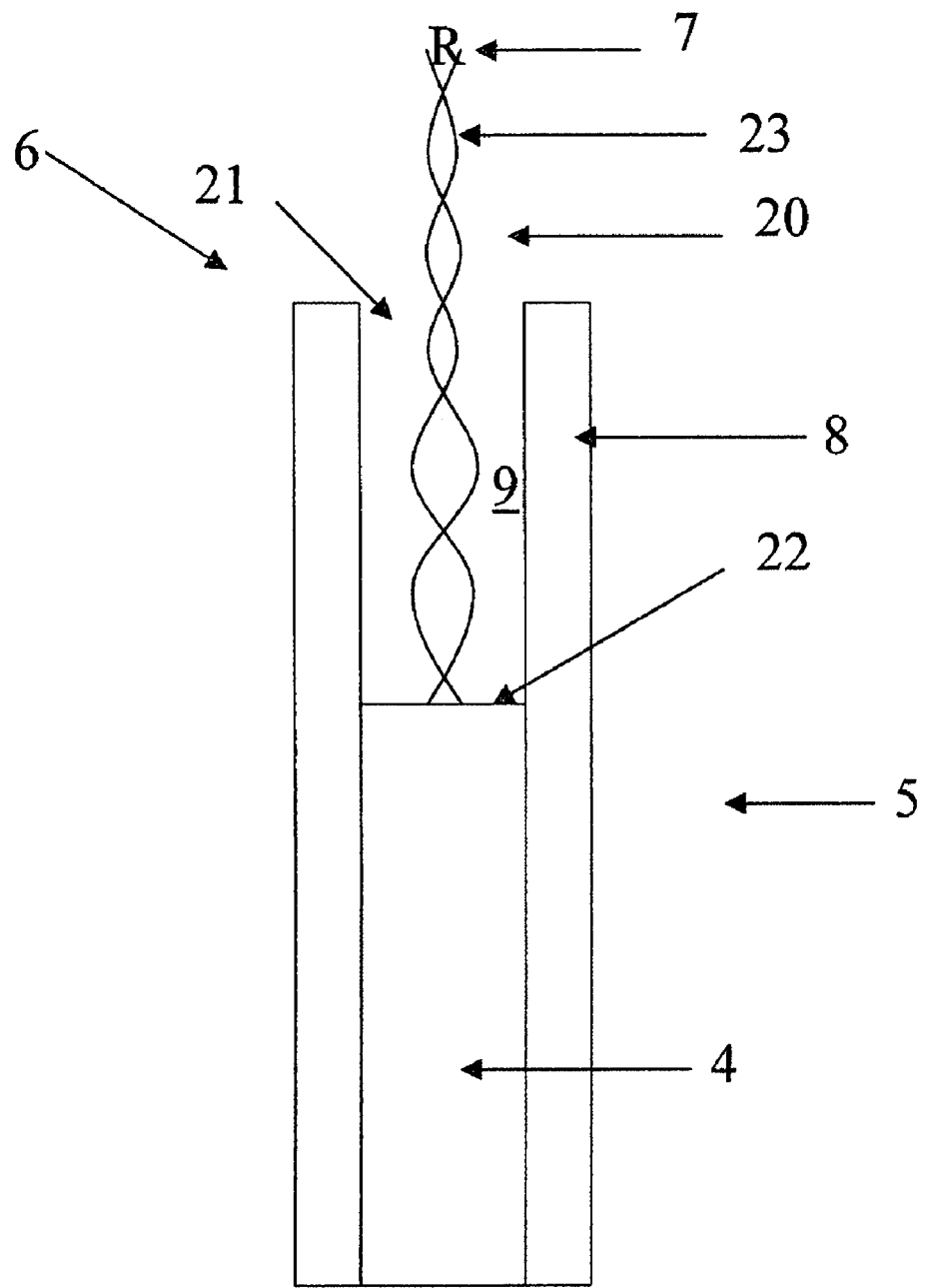
FIG. 3 depicts a side cross sectional view of one embodiment of a probe including a tether for extracting molecular material from a cell, in accordance with the present invention.

FIG. 3 depicts one embodiment of a probe 5 including a tether 20 composed of a linear chain molecule (hereafter referred to as linear chain molecule tether 23) for extracting target molecular material from a cell, in accordance with the present invention. In one embodiment, the probe 5 is of a partial pipe construction and may include a carbon nano-fiber core 4 having a dielectric cylinder 8 present on the exterior sidewall surfaces of the carbon nano-fiber core 4. In one embodiment, the dielectric cylinder 8 has an opening 21 that extends to a surface 22 (also referred to a recessed surface) of the carbon nano-fiber core 4, wherein the sidewalls of the dielectric cylinder 8 and the recessed surface 22 of the carbon nano-fiber core 4 define a cavity 9.

In one embodiment, the linear chain molecule tether 23 is connected to the surface 22 of the carbon nano-fiber core 4 that is within the cavity 9. In one embodiment, the linear chain molecule tether 23 is composed a peptide nucleic acid (PNA) having a chemical backbone of N-(2-aminoethyl)-glycine units linked by peptide bonds and bases linked to the backbone by methylene carbonyl bonds, wherein the bases comprise purine, pyrimidine or combinations thereof. In one embodiment the end of the linear chain molecule tether 23 connected to the surface 22 of the carbon nano-fiber core 4 is opposite the end of the linear chain molecule tether 20 on which the receptor 7 is position.

In one embodiment, linear chain molecule tether 23 is ionically charged of a first type charge, e.g, negative charge, wherein applying a voltage potential to the carbon nano-fiber core 4 to produce a substantially same type charge, e.g., negative charge, as the charge of the linear chain molecule tether 23 positions a portion of the linear chain molecule tether 23 to an exterior of the cavity 9. In another embodiment, applying a voltage potential to the carbon nano-fiber core 4 to produce a substantially opposing charge to the charge of the linear chain molecule tether 23 positions the linear chain molecule tether 23 within the cavity 9.

Figure 4A:
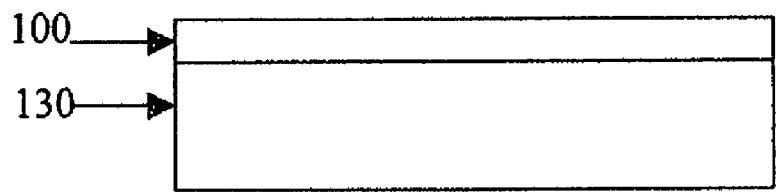
FIGS. 4A-4H depict one embodiment of a method for forming the probe depicted in FIG. 3, in accordance with the present invention.

FIGS. 4A-4H depict one embodiment of a method for forming the probe 5 depicted in FIG. 3. FIG. 4A depicts one embodiment of forming a membrane 100 composed of $Si_3N_4$ to provide a substrate. More specifically, in one embodiment, a silicon nitride membrane 100 is deposited on both sides of a silicon wafer 130 by chemical vapor deposition (CVD). In a following process step, windows are opened in the silicon nitride membrane 100 using photolithography and etch processes, such as $SF_6$ plasma etching utilizing a photoresist mask that is formed on the back side of the wafer 130. The wafer 130 is then etched in KOH stopping on the silicon nitride membrane 100.

Figure 4B:
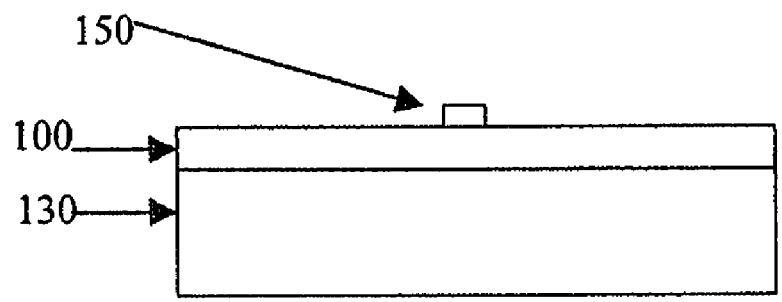

FIG. 4B depicts one embodiment of Ni catalyst sites 150 being created using e-beam lithography and lift-off techniques. More specifically, in one embodiment, electron beam lithography is utilized to define Ni catalyst sites 150 for growth of vertically aligned carbon nano-fibers. In one embodiment, the Ni catalyst sites 150 are deposited using a lift off method, wherein an electron beam resist, such as poly(methyl-methocrylate) (PMMA), is deposited atop the membrane 100 and patterns (10 μm spaced dots on a square grid) were exposed and developed. In a following process step, the catalyst metal (Ni, 100 Å) was deposited by electron gun physical vapor deposition (PVD). Following catalyst deposition, the unexposed portions of the resist were then dissolved in acetone so that the catalyst metal remained only on the exposed (free from the resist) dots.

Figure 4C:
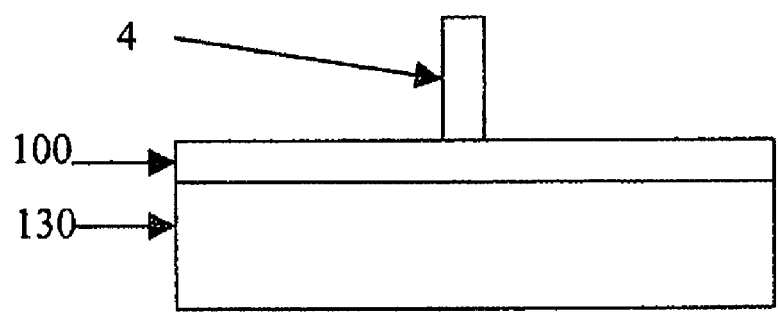

FIG. 4C depict one embodiment of growing a carbon nano-fiber core 4. In one embodiment, the carbon nano-fiber core 4 is grown in the glow discharge dc plasma including an ammonia/acetylene gas mixture at a temperature of about 700° C., with 2.5 Torr total pressure and 150 mA dc current.

Figure 4D:
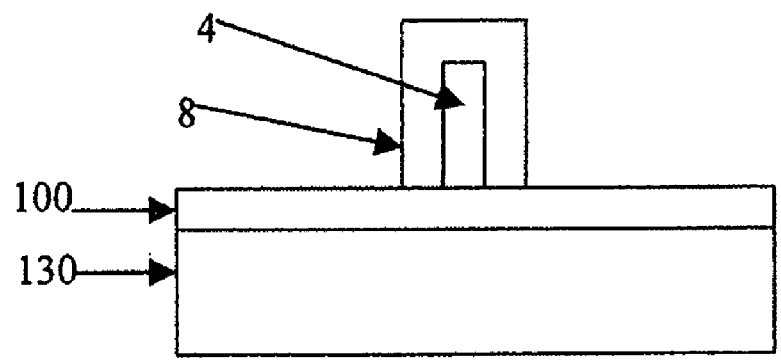

FIG. 4D depicts one embodiment of forming the dielectric cylinder 8 positioned on the exterior surface of the sidewalls of the carbon nano-fiber core 4 by coating the carbon nano-fiber core 4 and chip surface with a 100-nm-thick layer of $SiO_2$ using a silane-based plasma enhanced chemical vapor deposition process.

Figure 4E:
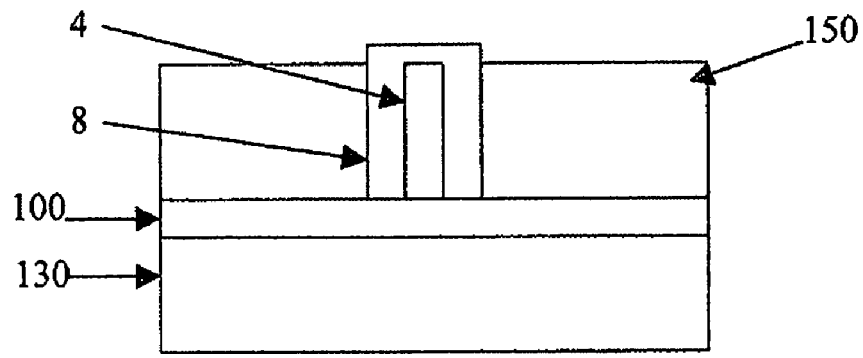

FIG. 4E depicts on embodiment of forming a photoresist mask 150 to expose the upper surface of the dielectric cylinder 8, wherein the upper surface of the dielectric cylinder 8 is removed by a reaction ion etching. In one embodiment, the photoresist mask 150 is provided by depositing resist over the surface of the chip by spin deposition, wherein the thickness is adjusted using reactive ion etching (RIE) in oxygen plasma to uncover the upper surface of the dielectric cylinder 8.

Figure 4F:
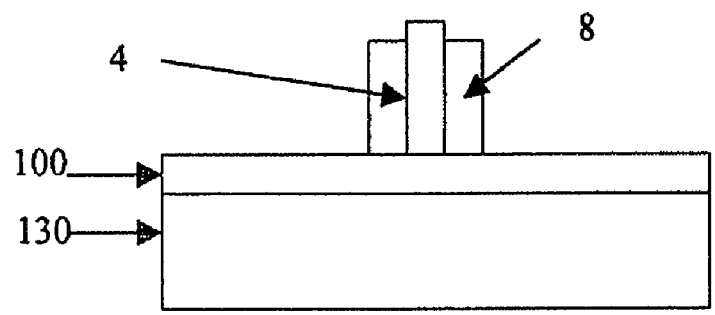

Referring to FIG. 4F, in a following process step, the silicon oxide may be removed from exposed upper surface of the dielectric cylinder 8 using a reactive ion etch in $CHF_3/O_2$ RF (radio frequency) plasma. Following etch of the upper surface of the dielectric cylinders 8, the photoresist mask 150 may then be removed. In one embodiment, the removal of the photoresist mask 150 included dissolving the photoresist in acetone or, alternatively, etching the photoresist mask 150 in a RIE oxygen-based plasma. The latter method is preferable since it uncovered the catalyst particle from the carbon film that covered it after VACNF growth.

Figure 4G:
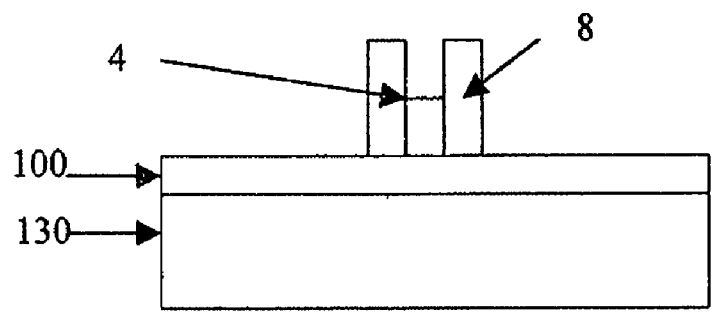

FIG. 4G depicts recessing the exposed surface of the carbon nano-fiber core 4 within the dielectric cylinder 8. In one embodiment, recessing of the exposed surface of the carbon nano-fiber core 4 includes reactive ion etching (RIE). In one embodiment, the reactive ion etch process includes an etch chemistry for removing carbon selective to oxide. In one embodiment, the reactive ion etch process is a timed etch, wherein the etch time is selected to provide a cavity having dimensions to house a tether 20, in accordance with the present invention.

Figure 4H:
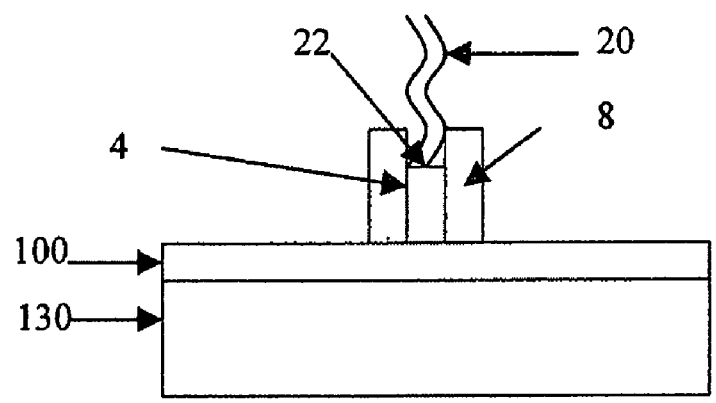

FIG. 4H depicts forming a tether 20 engaged to the recessed surface 22 of the carbon nano-fiber core 4. As discussed above, the tether 20 may be composed of a linear chain molecule, such as DNA or RNA. In one embodiment, the tether 20 is engaged to the carbon nano-fiber core 4 by an amine bonded through carboxyl groups to the recessed surface 22 of the carbon nano-fiber core 4, which is contained within the cavity and is exposed by the opening 21 of the dielectric cylinder 8.

While the present invention has been particularly shown and described with respect to the preferred embodiments thereof, it will be understood by those skilled in the art that the foregoing and other changes in forms of details may be made without departing form the spirit and scope of the present invention. It is therefore intended that the present invention not be limited to the exact forms and details described and illustrated, but fall within the scope of the appended claims.

What is claimed:

1. A probe for extracting molecular material from a sample containing said molecular material, the probe comprising:
   (a) a dielectric cylinder having (i) an opening and (ii) a cavity extending from said opening through a length of said cylinder;
   (b) a carbon nano-fiber recessed from the opening of the cylinder to a position inside the dielectric cylinder cavity, thereby forming a carbon nano-fiber core; and
   (c) a tether comprising a receptor for said molecular material, wherein the tether comprises DNA, RNA, a protein, peptide nucleic acid (PNA), and combinations thereof, and wherein the tether is covalently attached to a surface of the carbon nano-fiber core; and wherein the tether has a first charge,
   wherein by applying a second charge to the carbon nano-fiber core:
   (i) when said first and said second charge are the same charge polarity then a portion of the tether extends to an exterior of the cavity; and/or
   (ii) when said first and said second charge are of the opposite charge polarity then a portion of the tether extended exterior of the cavity positions the tether within the cavity.

2. The probe of claim 1, wherein the dielectric cylinder comprises an oxide.

3. The probe of claim 1, wherein the dielectric cylinder has a radial dimension of less than about 300 nm, and the length of the probe is less than about 100 microns.

4. The probe of claim 1, wherein the tether comprises a peptide nucleic acid (PNA) comprising a chemical backbone of N-(2-aminoethyl)-glycine units linked by peptide bonds and bases linked to the chemical backbone by methylene carbonyl bonds, wherein the bases comprise purine, pyrimidine or combinations thereof.

5. The probe of claim 1, wherein the receptor is positioned along an entire length of the tether.

6. A method for extracting molecular material comprising:
   providing a probe according to claim 1, wherein the probe comprises a penetration portion having a nanoscale surface for penetrating a biological compartment, a receptor present on the penetrating portion of the probe, wherein the receptor has an affinity for a target molecular material;
   inserting the probe into the biological compartment, wherein the receptor present on the penetrating portion of the probe engages the target molecular material; and
   extracting the probe and the target molecular material engaged to the receptor present on the penetrating portion of the probe from the biological compartment.

7. The method of claim 6, wherein the receptor comprises DNA, proteins, RNA, peptide nucleic acids, or combinations thereof.

8. The method of claim 6, wherein the receptor comprises poly T oligo, and the target molecular material is at least one polyadenylated mRNA.

9. The method of claim 6, wherein the receptor comprises a tetR protein and the target molecular material comprises a tetO operator.

10. The method of claim 6, wherein the receptor comprises Gamma-H2AX and the target molecular material comprises dsDNA.

11. The method of claim 6, wherein the receptor comprises an Anti-Tubulin antibody and the target molecular material comprises tubulin.

12. The method of claim 6, wherein the receptor comprises an Anti-p53 antibody and the target molecular material comprises p53 or p53 mutants.

13. A method for extracting molecular material comprising:
   providing a probe according to claim 1, wherein the probe comprises a penetration portion comprising a nanoscale surface for penetrating a biological compartment, the penetration portion including the cavity and the tether, the tether including receptor having an affinity for a target molecular material, wherein a surface of the tether has said first charge;
   inserting at least the penetrating portion of the probe through a membrane of the biological compartment;
   applying a first potential to the probe, the applied first potential producing a substantially same charge as the tether surface first charge, thereby extending at least a portion of the tether to an exterior of the cavity, wherein the receptor engages the target molecular material;
   applying a second potential to the probe, the applied second potential producing a substantially opposing charge as the tether surface first charge, thereby retracting within the cavity at least a portion of the tether and the target molecular material engaged to the receptor; and
   extracting the probe and the target molecular material engaged to the receptor of the probe from the biological compartment.

14. The method of claim 13, wherein the tether comprises a linear chain molecule or a linear molecular array.

15. The method of claim 13 further comprising applying the second type potential to the probe to retract the tether within the cavity prior to the inserting of the at least the penetrating portion of the probe into the biological compartment.

16. The method of claim 13, wherein the receptor is reversibly connected to the penetrating portion of the probe by a cleavable linkage group.

17. The method of claim 15, wherein the cleavable linkage group is provided by a disulfide bond.

18. The method of claim 16, wherein the tether further comprises a nuclear localization signal.

* * * * *

SEQUENCE LISTING

```
<160> NUMBER OF SEQ ID NOS: 3

<210> SEQ ID NO 1
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 1

Pro Lys Lys Lys Arg Lys Val
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 2

Ala Pro Thr Lys Arg Lys
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 3

Arg Lys Leu Lys Arg
1               5
```